(12) United States Patent
Rogers

(10) Patent No.: US 9,232,304 B2
(45) Date of Patent: Jan. 5, 2016

(54) EAR CANAL SEALING STETHOSCOPE EAR TIPS

(71) Applicant: 3M INNOVATIVE PROPERTIES COMPANY, St. Paul, MN (US)

(72) Inventor: Daniel J. Rogers, Grant, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 126 days.

(21) Appl. No.: 14/136,970

(22) Filed: Dec. 20, 2013

(65) Prior Publication Data
US 2015/0181330 A1    Jun. 25, 2015

(51) Int. Cl.
H04R 1/46     (2006.01)
H04R 1/10     (2006.01)
A61B 7/02     (2006.01)

(52) U.S. Cl.
CPC .. *H04R 1/46* (2013.01); *A61B 7/02* (2013.01); *H04R 1/1016* (2013.01)

(58) Field of Classification Search
None
See application file for complete search history.

(56) References Cited

U.S. PATENT DOCUMENTS

| 1,045,812 | A | 12/1912 | Campbell |
|---|---|---|---|
| 1,863,474 | A | 1/1933 | Lieber |
| 2,220,208 | A | 11/1940 | Cannon |
| 2,650,633 | A | 9/1953 | Eger |
| 2,934,160 | A | 4/1960 | Touson |
| 3,169,600 | A | 2/1965 | Thomas |
| 3,303,902 | A | 2/1967 | Knott |
| 3,539,031 | A | 11/1970 | Scanlon |
| 3,618,600 | A | 11/1971 | Douglass |
| 3,710,888 | A | 1/1973 | Peart |
| 3,768,470 | A | 10/1973 | Leight |
| 3,895,627 | A | 7/1975 | Leight |
| 3,896,801 | A | 7/1975 | Grout |
| 4,055,233 | A | 10/1977 | Huntress |
| 4,089,332 | A | 5/1978 | Rose |
| 4,311,206 | A | 1/1982 | Johnson |
| 4,434,794 | A | 3/1984 | Leight |
| 4,552,137 | A | 11/1985 | Strauss |
| 4,564,009 | A | 1/1986 | Brinkhoff |
| 4,852,684 | A | 8/1989 | Packard |
| D304,722 | S | 11/1989 | Hashimoto |
| 5,288,953 | A | 2/1994 | Peart |
| 5,449,685 | A | 9/1995 | Patel |

(Continued)

FOREIGN PATENT DOCUMENTS

GB    2173110    2/1986

OTHER PUBLICATIONS

International Search Report for International Publication No. PCT/US2014/069542, dated Mar. 6, 2015.

*Primary Examiner* — Paul Huber

(57) ABSTRACT

An ear tip is adapted to deliver sound to an ear canal. The ear tip includes a first section, a second section and a third section. The first section is connectable to a sound-transmitting device. The second section has a first end, a second end and walls defining a bulbous section. The first end is connected to and in open communication with the first section. The second end is connected to and in open communication with the third section. The third section includes walls defining a flume and an outlet port adapted for open communication with the ear canal. The outlet port has a maximum outer diameter of about 11 millimeters. In a relaxed state, a ratio of a maximum outer diameter of the second section to a maximum diameter of the third section is between about 1.25 and about 2.5.

21 Claims, 8 Drawing Sheets

(56) References Cited

U.S. PATENT DOCUMENTS

| | | |
|---|---|---|
| 5,474,571 A | 12/1995 | Lang |
| 5,824,968 A | 10/1998 | Packard |
| 6,129,174 A | 10/2000 | Brown |
| 6,513,621 B1 | 2/2003 | Deslauriers |
| 6,860,362 B2 | 3/2005 | Saltykov |
| 7,506,720 B1 | 3/2009 | Hicks |
| 8,265,323 B2 | 9/2012 | Stiehl |
| 8,280,093 B2 | 10/2012 | Siahaan |
| 8,638,970 B2 | 1/2014 | Burton |
| 2011/0079228 A1 | 4/2011 | Maloney |

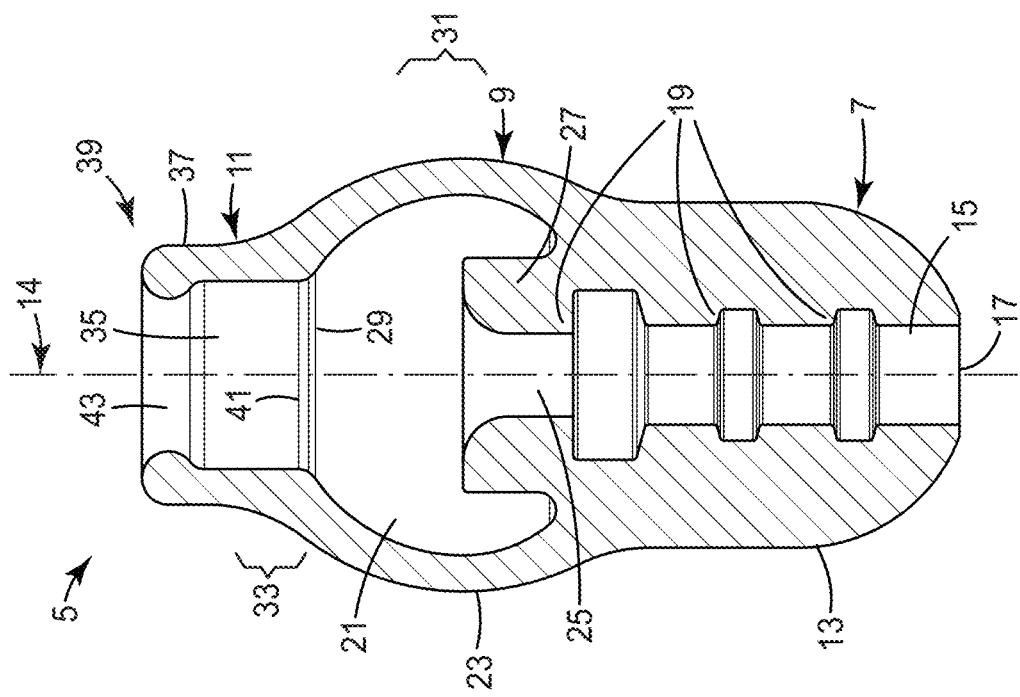
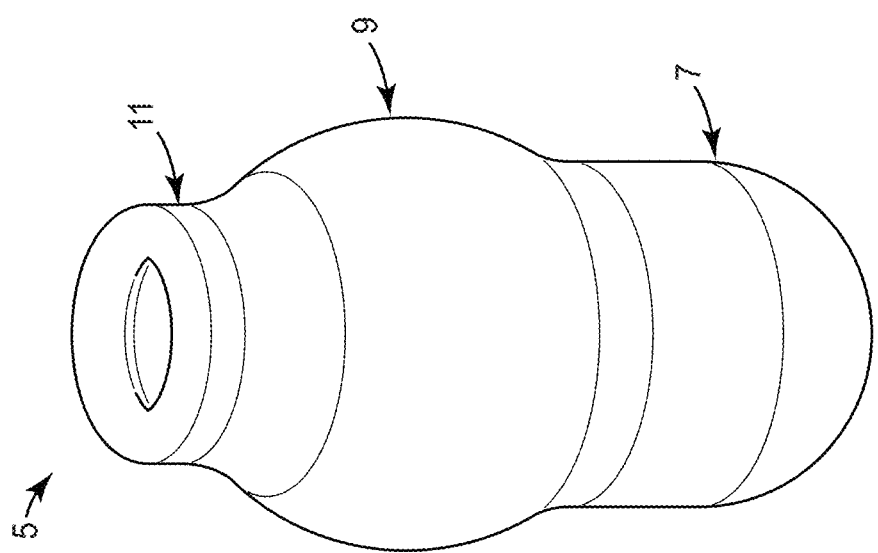

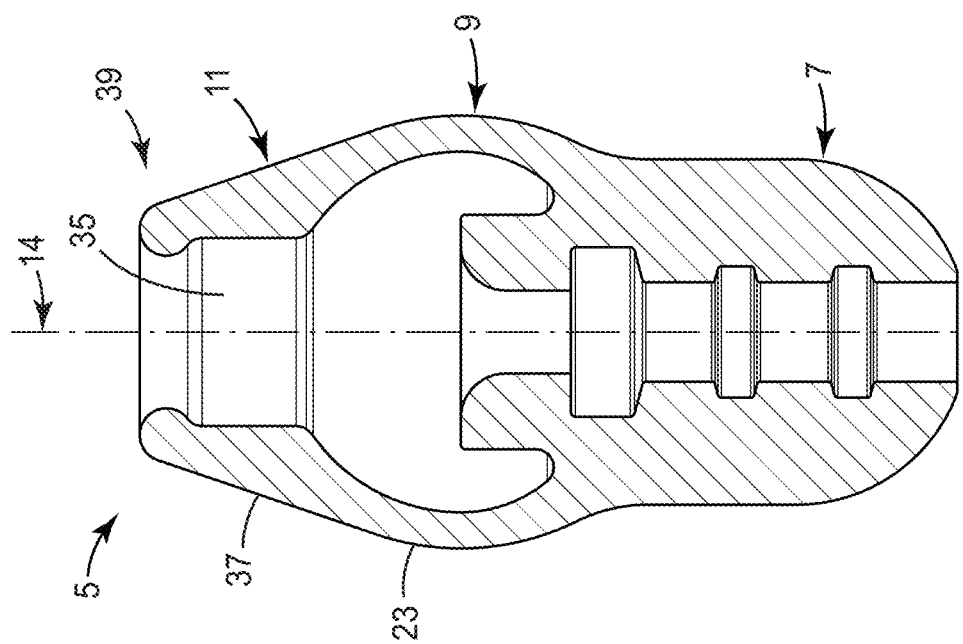
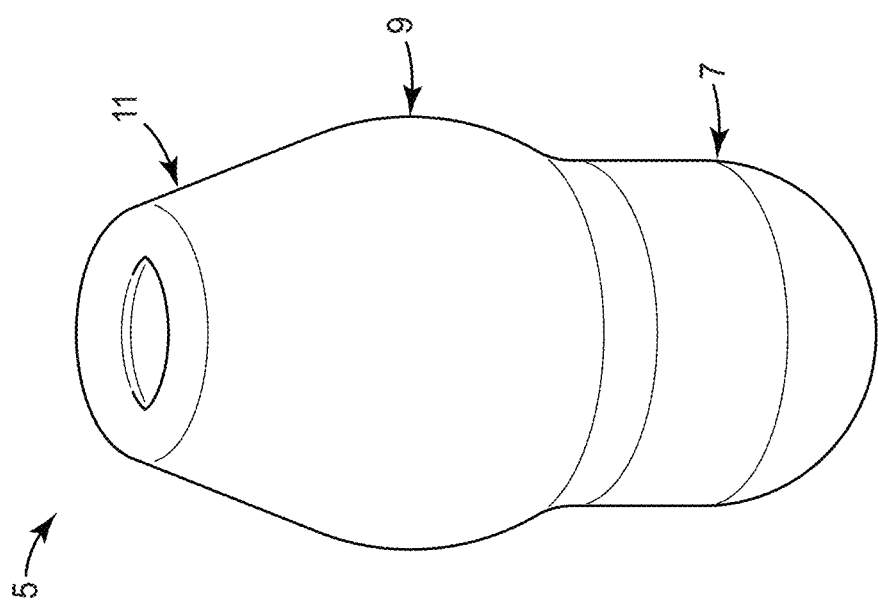

EAR CANAL SEALING STETHOSCOPE EAR TIPS

TECHNICAL FIELD

The present invention is related generally to the field of ear tips for stethoscopes. In particular, the present invention is an ear tip for stethoscopes that provides an enhanced acoustic seal and comfort.

BACKGROUND

Among the myriad devices employing ear tips, stethoscopes and audio headsets are among the most common. Some stethoscopes may employ a spring-loaded means for forcing the ear tips into the user's ears in an attempt to create a sound-proof seal that maximizes the wearer's ability to hear only the desired sound free of ambient interference. This general design creates two related problems for the user. First, the exterior ear canal is rather sensitive to pressure and second, the ear canal varies in size and shape from person to person. Thus, hard conventional ear tips can cause serious discomfort by applying high pressure to the irregular surface of the user's ear canal. Furthermore, such hard ear tips form a poor acoustic seal with the ear, allowing ambient sound to infiltrate the ear canal and obscure the sound delivered by the device.

These problems of comfort and sound exclusion have been addressed in a number of ways, both as to ear tips and as to ear plugs. For example, soft, malleable materials such as air encased in a plastic bladder (U.S. Pat. Nos. 3,895,627, 3,768, 470, and 4,089,332), a mushroom shaped soft rubber head (U.S. Pat. No. 3,618,600), malleable plastic (U.S. Pat. No. 4,552,137), and closed-cell foam encased in a plastic shell (U.S. Pat. No. 4,434,794) are described in the patent literature.

Design variations such as a flared, horn-shaped ear tip designed to fit over, rather than into, the ear canal (U.S. Pat. No. 3,303,902), various shapes with skirt-like flanges that insert into the ear canal (U.S. Pat. Nos. 4,564,009 and 3,896, 801, G.B. patent No. 2,173,110 A), and soft mushroom-shaped ear tips (U.S. Pat. Nos. 4,055,233 and 3,539,031) have appeared as well. All such inventions rely upon pressure to create a good acoustic seal.

A further design, appearing in U.S. Pat. No. 4,552,137, teaches a solution where a tight fit is attained not by pressure but by a layer of adhesive on the ear tip's surface.

SUMMARY

In one embodiment, the present invention is an ear tip adapted to deliver sound to an ear canal. The ear tip includes a first section, a second section and a third section. The first section is connectable to a sound-transmitting device. The second section has a first end, a second end and walls defining a hollow bulbous section. The first end is connected to and in open communication with the first section. The second end is connected to and in open communication with the third section. The third section includes walls defining a flume and an outlet port adapted for open communication with the ear canal. The outlet port has a maximum outer diameter of about 11 mm. In a relaxed state, a ratio of a maximum outer diameter of the second section to a maximum outer diameter of the third section is between about 1.25 and about 2.5.

In another embodiment, the present invention is an ear tip including a first section, a second section and a third section. The first section is connectable to a sound-transmitting device. The second section has a first end, a second end and walls defining a hollow bulbous section surrounding an inner chamber. The first end is connected to and in open communication with the first section. The second end is connected to and in open communication with the third section. The third section includes walls defining a flume having a tip positionable within a human ear canal. The second and third sections are deformable under an axial force in a range of between about 2.22 to about 5.56 Newtons from a relaxed state to a compressed state. The flume tip exhibits a compression diameter increase of up to 50%.

BRIEF DESCRIPTION OF DRAWINGS

FIG. 2A is a perspective view of a first embodiment of the ear tip in the relaxed state.

FIG. 2B is a cross-sectional view of the first embodiment of the ear tip in the relaxed state.

FIG. 3A is a perspective view of a second embodiment of the ear tip in the relaxed state.

FIG. 3B is a cross-sectional view of the second embodiment of the ear tip in the relaxed state.

These figures are not drawn to scale and are intended merely for illustrative purposes.

DETAILED DESCRIPTION

Figure 1:
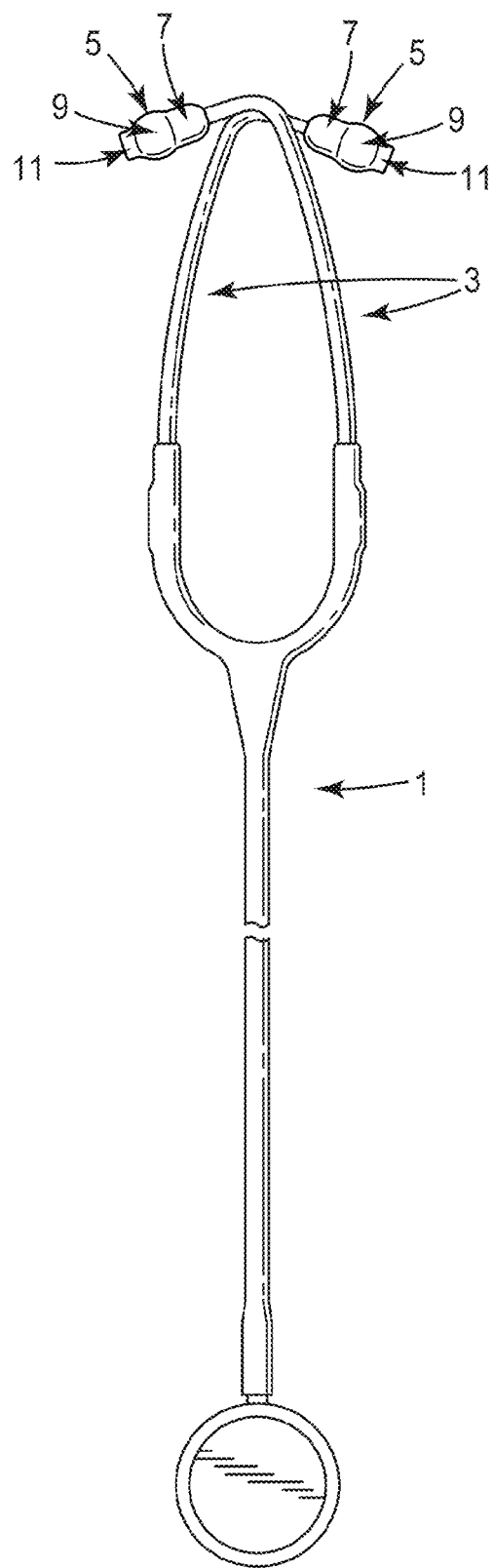
FIG. 1 is a plan view of a stethoscope equipped with ear tips of the present invention.

Referring to FIG. 1, a spring-loaded stethoscope 1 is shown having dual sound-transmitting tubes 3 each terminating in ear tips 5. A first embodiment of the ear tip 5 of the present invention is shown in FIGS. 2A and 2B in a relaxed or non-compressed state. FIG. 2A shows a perspective view of the ear tip and FIG. 2B shows a cross-sectional view. Ear tip 5 is composed of three major sections, a first section 7 to which the tubes 3 (FIG. 1) are attached, a second, middle section 9 in contact with the ear when in use and a third section 11 that serves as the terminus of stethoscope 1 (shown in FIG. 1) and that is positionable within the ear canal. In one embodiment, section 7 has a generally cylindrical, symmetrical shape formed of first section walls 13 defining an axial extending central channel 15 adapted to receive tube 3 (shown in FIG. 1) in frictional-fitting relationship. Interior of opening 17 of channel 15 are spaced-apart shoulders 19 that serve as a stop against which the end of tube 3 abuts.

Channel 15 communicates with hollow inner chamber 21 of second section 9 defined by second section walls 23. Second section walls 23 are relatively thin throughout, such that the ratio of (i) the inside diameter of the second section 9 measured in the region of greatest outside diameter of the second section 9 to (ii) the greatest outside diameter of the second section 9 is between about 0.6 and 0.95, particularly between about 0.8 and 0.95. Second section walls 23 extend from junction with first section walls 13 outwardly for a distance and then inwardly thereafter with reference to the axis in a smooth, continuously curved, symmetrical fashion providing a generally bulbous second section with an inner surface that is convex relative to the inside of hollow inner chamber 21 and defines hollow inner chamber 21.

In one embodiment, the bulbous second section 9 has a maximum outer diameter of greater than about 10 millimeter (mm) (about 0.4 inches). In particular, the bulbous second section 9 has a maximum outer diameter of between about 10 and 14 mm (about 0.4 and about 0.55 inches). When the bulbous second section 9 is compressed, for example when the ear tip 5 is inserted into the ear under the spring force of the stethoscope tubing, the outer diameter of the bulbous section 9 increases by greater than about 10%. The force required to compress or collapse the bulbous second section 9 is between about 2.22 to about 5.56 Newtons (about 8 to about 20 ounces).

Chamber 21 of second section 9 includes an entry port 25 defined by a short cylindrical stop 27 that projects into chamber 21 a predetermined distance to provide a stop means to prevent extensive inward compression of second section walls 23. Cylindrical stop 27 does not, however, project so far into chamber 21 that axial compression of the second section walls is totally prevented. Second section walls 23 terminate to define a connection port 29 of circular cross-section. Connection port 29 is not integral with cylindrical stop 27, since such a construction would prevent the desired compression of the ear tip 5. To prevent occlusion of the connection port 29 upon compression of the ear tip 6, connection port 29 has a diameter of at least about 2.5 mm about (0.1 inches), and particularly about 3.8 mm (about 0.15 inches).

As can be seen in the embodiment of the ear tip 5 shown in FIG. 2B, the thickness of second section walls 23 varies from a minimum thickness generally in the region 31 of the greatest outside diameter of second section 9, to a maximum thickness nearest the region 33, which defines connection port 29. In one embodiment, the thickness of walls 23 gradually increases from the minimum to the maximum. This construction permits the second section 9 to flex in the region 31 of minimum thickness under the pressures exerted by spring-loaded stethoscopes causing second section 9 to bulge outwardly, as shown in FIG. 4.

Channel 15 and hollow inner chamber 21 of second section 9 communicate with hollow inner chamber 35 of third section 11 defined by third section walls 37. Similar to second section walls 23, third section walls 37 are relatively thin throughout, such that the ratio of (i) the inside diameter of the third section 11 measured in the region of greatest outside diameter of the third section 11 to (ii) the greatest outside diameter of the third section 11 is between about 0.5 and 0.9, particularly between about 0.6 and 0.8. Third section walls 37 extend from the junction (region 33) with second section walls 23 inwardly for a distance with a decreasing slope curvature with reference to the axis 14 in a smooth, continuous fashion, providing a flume shaped third section 39 with an inner surface that defines hollow inner chamber 35. Although FIGS. 2A and 2B depict the flume 39 as having a relatively steep initial slope, third section walls 37 may have a more gradual slope and may be more linear than curved, as depicted in FIGS. 3A and 3B. In fact, the curvature of the transition between the exterior of second section walls 23 and third section walls 37 may be concave, convex or straight, without departing from the intended scope of the present invention. In one embodiment, the flumed shaped third section 11 has a length of between about 2.54 and about 6.35 mm (about 0.1 and about 0.25 inches). Chamber 35 includes an entry port 41, which is concurrent with the connection port 29 of chamber 21. Chamber 35 also has an outlet port 43. The outlet port 43 is at or proximate the tip of the flume 39. In one embodiment, the entry port 41 has an inner diameter of greater than about 2.5 mm (about 0.1 inches). In particular, the entry port 41 has an inner diameter of between about 2.5 and about 7 mm (about 0.1 and about 0.275 inches). Third section walls 37 terminate to define the outlet port 43 of circular cross-section for positioning within the auditory canal. In one embodiment, the outlet port 43 has a maximum outer diameter of greater than about 5.6 mm (about 0.22 inches) and less than about 11 mm (about 0.4 inches). In one embodiment, the outlet port 43 has an inner diameter of between about 5.6 and about 11 mm (about 0.22 and about 0.4 inches). In one embodiment, the ratio of (i) the greatest outside diameter of the second section 9 to (ii) the greatest outside diameter of the third section 11 is between about 1.25 and about 2.5 and particularly about 1.5. To prevent occlusion of the port upon compression of the ear tip, outlet port 43 has a diameter of at least about 2.5 mm (about 0.1 inches), particularly about 3.8 mm (about 0.15 inches).

Figure 4:
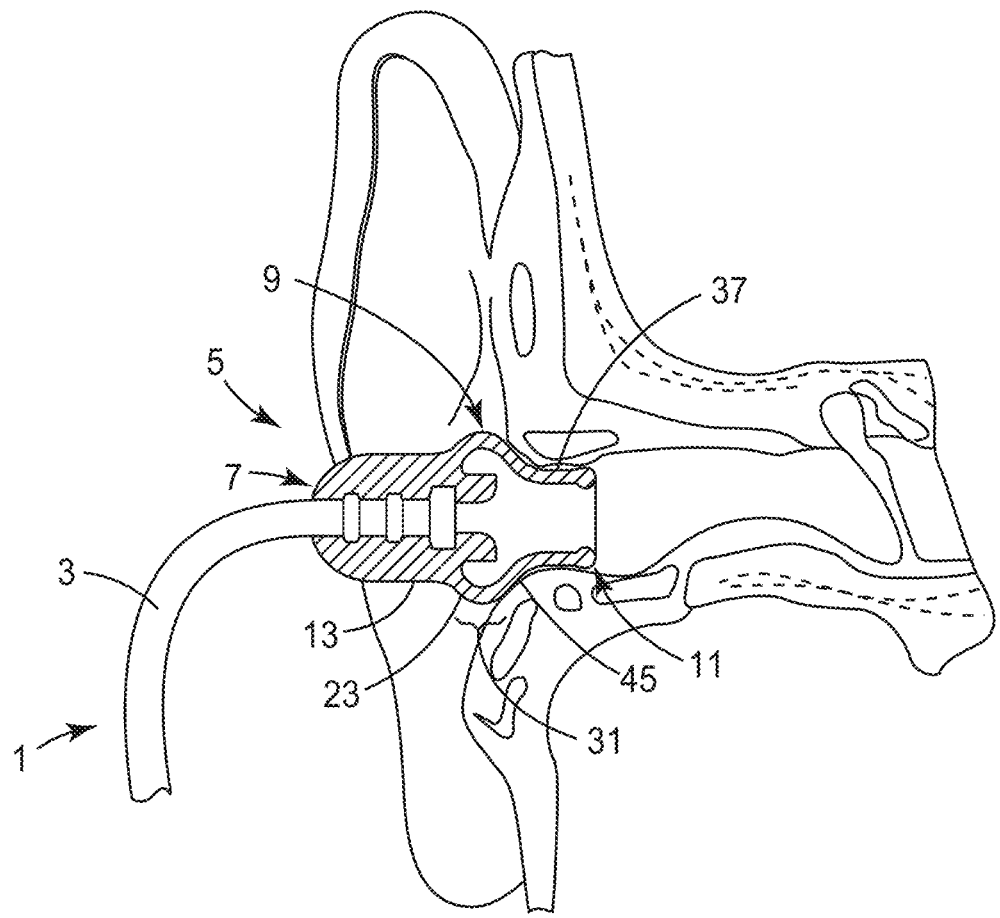
FIG. 4 is a plan view of the ear tip of FIG. 2A shown in its compressed state in the ear.

In FIG. 4, ear tip 5 is shown in its compressed state upon being forced against external acoustic meatus 45 of the human ear by pressure exerted through tube 3 of stethoscope 1. The first and second sections 7 and 9 of the ear tip 5 do not penetrate into the ear canal. Rather, the second section walls 23 flex in region 31 causing the walls to bulge, presenting a relatively large surface contact area to the external acoustic meatus 45. Spreading the force exerted by the stethoscope over a large area provides the enhanced comfort exhibited by the ear tip 5 of the invention. Moreover, owing to the soft, elastic nature of the second section walls 23, the second section walls 23 are seen to conform closely to the irregular surface and slightly oval shape of the external acoustic meatus 45.

Third section 11 of the ear tip 5 does enter the ear canal opening and together with second section 9, provides an acoustic seal. The result is substantial exclusion of ambient noise, which along with comfort is a critical requirement for a stethoscopic ear tip, providing a solution to the original problem of comfort and sound exclusion presented above.

To achieve the compression characteristics of the ear tip 5, the second and third section walls 23 and 37 should be composed of a soft, elastic or elastomeric material, which is compliant enough to compress and partially change shape yet resilient enough to not completely collapse and occlude the acoustic port. In one embodiment, the material is non-porous. Suitable materials include, but are not limited to: vulcanized natural rubber, vinyl elastomers, elastomeric polyurethanes, silicone rubbers, nitrile rubbers, and thermoplastic rubbers, such as are sold under the tradename Kraton G by the Shell Chemical Company. The second and third section walls 23 and 37 should also present a contact surface that is compatible with the area of the ear to which it will be exposed. Compatibility in this sense includes both resistance to the acidic oils present in the ear as well as low cytotoxicity.

As a practical matter, it is preferred that the entire ear tip 5 is constructed of a single material of the type described above. The ear tip 5 may be fabricated by a variety of conventional methods including, but not limited to: compression molding, transfer molding, liquid casting, and injection molding, particularly liquid injection molding. The latter method provides for lower unit cost for large quantities.

The force exerted by the stethoscope or other device, that is, the incoming force, is counterbalanced by a reactive force that can be resolved into two components, one parallel to the axis of the ear tips and one normal to that axis. The magnitude of those component forces depends upon disposition of the third section of the ear tip against the ear in the compressed state. The ear tip of the invention is constructed such that the reactive forces do not cause the ear tip to collapse or fold off its axis of symmetry; that is to say the ear tip is stable under conditions of use. This is accomplished by properly shaping the ear tip and by selecting materials of construction of the proper hardness.

As regards the shape of the ear tip, it is important that the ear tip not be necked down excessively such that the first section 7, or the area of interface between the first and second sections 7 and 9, has a much smaller outside diameter than does the second section 9 in the region 31. Such a necking down may cause the ear tip 5, when placed in the ear under the force of a stethoscope or like sound-transmitting device, to fold over off its axis of symmetry, with concomitant loss of open communication between the ear and the sound-transmitting device. On the other hand, if the second section walls 23 are not allowed to neck down somewhat between the region 31 and the first section 7, the second section walls 23 will not bulge properly in region 31 and comfort to the user will be sacrificed.

Proper bulging and stability of the ear tip are affected by internal dimensions as well as by external dimensions, that is, by the shape of the hollow chamber 21 as well as by the outside geometry of the ear tip. For present purposes, the dimensions of the hollow chamber 21 are (1) the greatest inside diameter, measured in region 31, and (2) the internal length, measured as the distance from the outside of the connection port 29, past the region of greatest outside diameter. If the hollow chamber 21 is too long relative to the greatest internal diameter, the stability of the ear tip 5 will be sacrificed. For optimal performance, it is desirable for the ratio of internal length: greatest internal diameter to be less than about 1.5, particularly less than about 1.2, and more particularly less than about 1.0. In one embodiment, the ratio is about 0.8.

As regards hardness, the harder the material, the thinner the wall should be in order for the ear tip to compress and spread properly under the load of the headset. The lower limit of Shore hardness is that which prevents the reactive forces from collapsing the second section in such a fashion that open communication between the first section and the ear canal is blocked. The geometry of the ear varies from individual to individual but as a practical matter a lower limit of about 10 A Shore hardness is suitable. On the upper end, a Shore hardness of about 90 A is considered suitable. At the present time, it appears that the preferred embodiment will be based on a hardness of 40 A to 60 A Shore hardness.

The wall thickness may typically vary from about 0.5 mm (about 0.02 inches) to about 1.5 mm (about 0.06 inches) in region 31 and in region 33, and may particularly be about 1 mm (about 0.04 inches) in region 31 and region 33. While walls of varying thickness are shown in FIGS. 2B, 3B and 5B, non-uniform wall thicknesses may be utilized without departing from the intended scope of the present invention, particularly at wall thicknesses in the range of above about 1.3 mm (about 0.05 inches).

While the ear tip is versatile as regards fitting in ears of various sizes and shapes, it may be desirable to vary the outside diameter of the second and third sections 9 and 11 to a degree in an effort to accommodate the very wide range of common ear canal sizes. In one embodiment, the outside diameter of the ear tip in the region 31 is at least about 10 mm (about 0.4 inches) to prevent deep penetration of the ear tip into the ear canal, and less than about 15.2 mm (about 0.6 inches) to assure that the ear tip will fit into the ear canal. In one embodiment, the maximum outside diameter in region 31 is about 12.2 mm (about 0.48 inches). When inserted into the ear canal, the third section 11 deforms into an oval shape, potentially causing the diameter of the third section 11 to increase in one direction. In one embodiment, the diameter of the third section 11 may increase up to about 50%. In one embodiment, the maximum oval diameter is between about 22% to about 25% larger than the circular diameter when deformed by insertion into the ear canal.

Figure 5B:
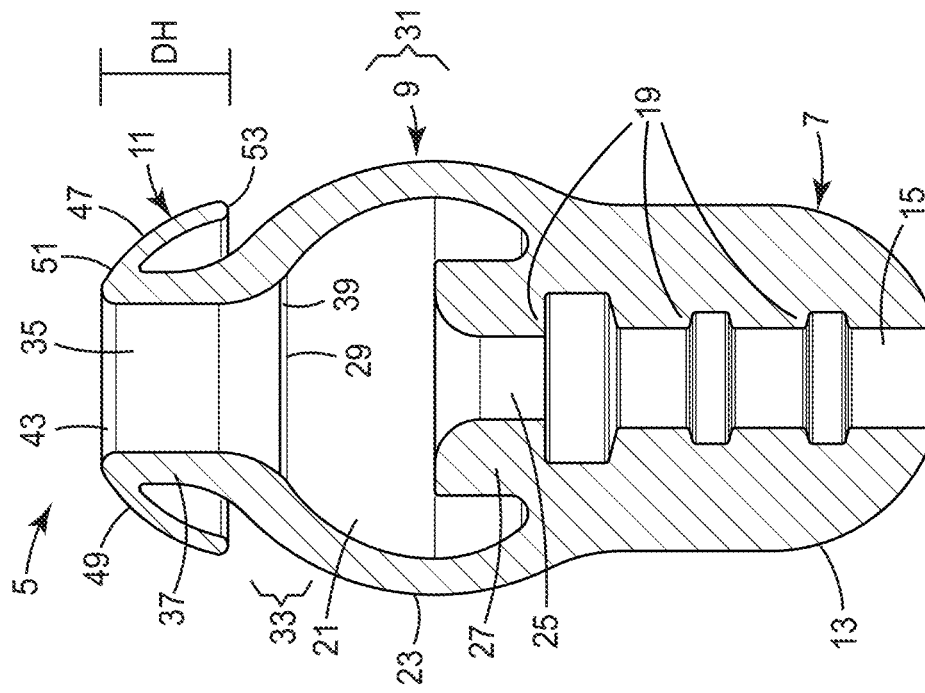
FIG. 5B is a cross-sectional view of the third embodiment of the ear tip in the relaxed state.
Figure 5A:
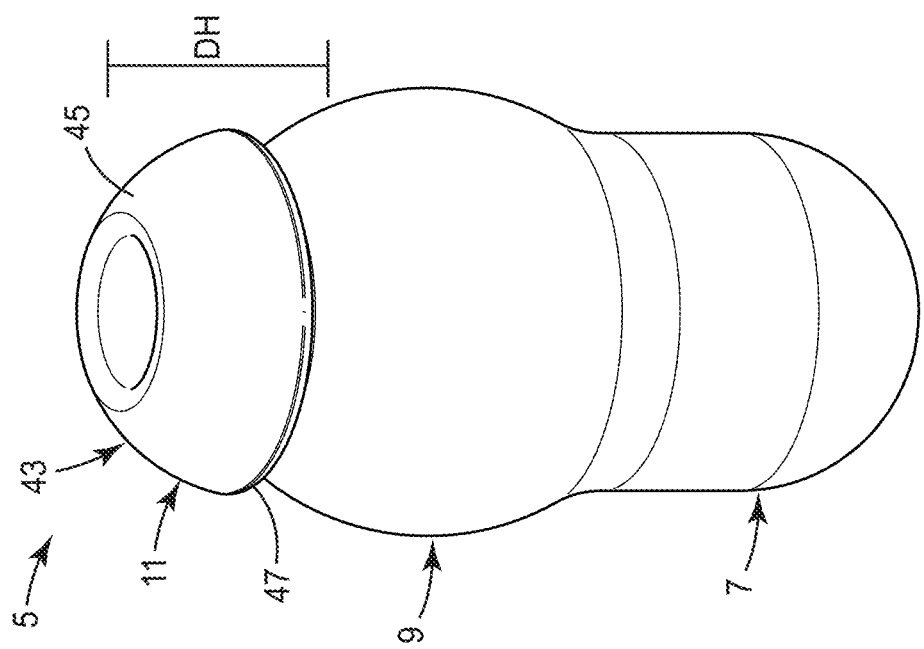
FIG. 5A is a perspective view of a third embodiment of the ear tip in the relaxed state.

A third embodiment of the ear tips 5 of the present invention are shown in FIGS. 5A and 5B, which show a perspective view and a cross-sectional view of the ear tip 5, respectively. The first, second and third sections 7, 9 and 11 of the third embodiment of the ear tip 5 are identical to the first and second embodiments of the ear tip 5 and function similarly except that the third section 11 of the third embodiment includes a flange 47 defined by flange walls 49 extending from the outlet port 43. The flange walls 49 first create a neck wall 51 where the second section wall 37 turns into the flange 47 at the outlet port 43. The flange 47 creates a dome shape that may be hemispherical or conical. The flange 47 has a thickness that allows it to be readily deformable for insertion into the ear canal to further reduce leakage of sound through the ear tips and provide an enhanced acoustic seal. In one embodiment, the flange wall 49 has a substantially uniform thickness. In another embodiment, the thickness of the flange wall 49 varies such that the flange wall 49 is thicker at the neck wall 51 so that the outlet port 41 does not pinch closed when inserted into the ear canal and under the spring force of the stethoscope tubes 3 (FIG. 1). In one embodiment, the flange wall 49 has a thickness of between about 0.3 and about 1.0 mm (about 0.01 and about 0.04 inches), particularly between about 0.4 and about 0.7 mm (about 0.016 and about 0.03 inches) and more particularly about 0.5 mm (about 0.02 inches) with the neck wall 51 having a thickness of between about 0.5 and about 1.5 mm (about 0.02 and about 0.06 inches), particularly between about 0.7 and about 1.2 mm (about 0.03 and about 0.05 inches) and more particularly between about 0.8 and about 1.0 mm (about 0.03 and about 0.04 inches). In one embodiment, the flange 47 has an outer diameter of between about 8.1 and about 13.2 mm (about 0.32 and about 0.52 inches) and particularly of about 10.2 mm (about 0.4 inches). The flange 47 includes a dome height DH, defined as the axial distance from the outlet port 41 of the third section 11 to an outer edge 53 of the flange 47. In one embodiment, the dome height DH is between about 4 and about 8 mm (about 0.15 and about 0.3 inches) and particularly of about 5.1 mm (about 0.2 inches).

Figure 6:
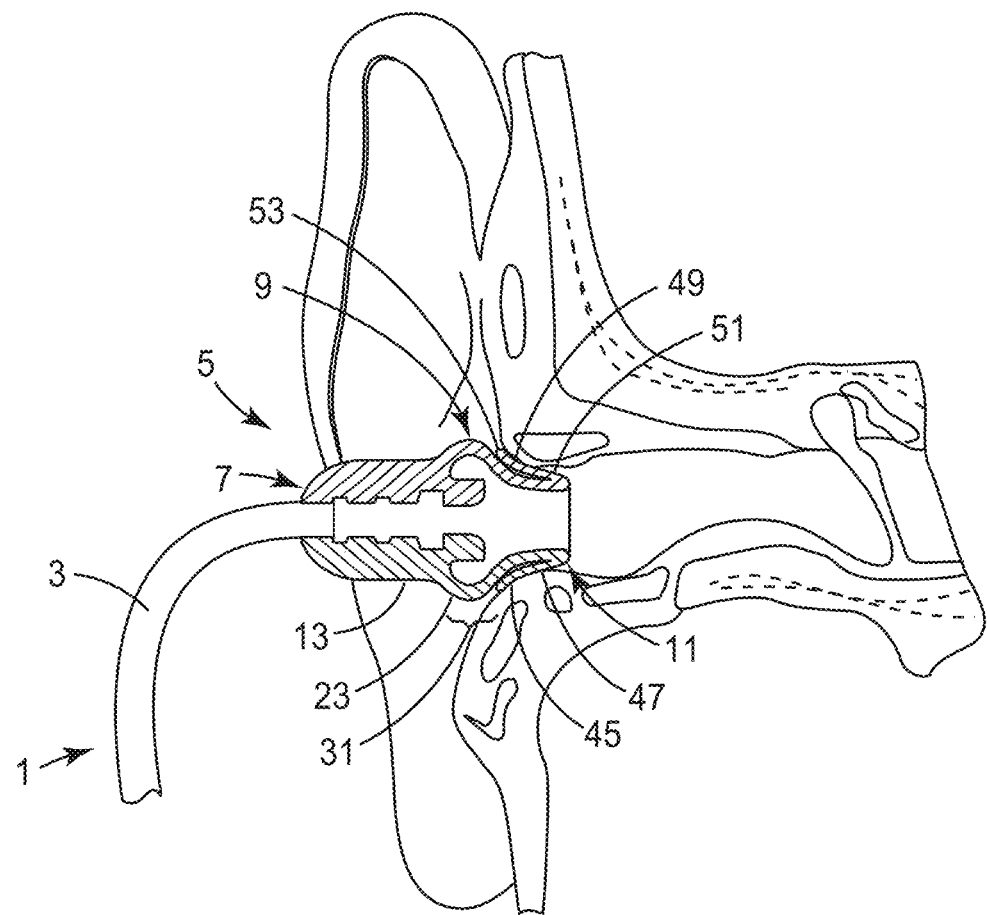
FIG. 6 is a plan view of the ear tip of FIG. 5A shown in its compressed state in the ear.

In FIG. 6, the third embodiment of the ear tip 5 is shown in its compressed state upon being forced against external acoustic meatus 45 of the human ear by pressure exerted through tube 3 of stethoscope 1. Similar to the first embodiment of the ear tip 5, the first and second sections 7 and 9 of the third embodiment of the ear tip 5 do not penetrate into the ear canal. Rather, the second section walls 23 flex in region 31 causing the walls to bulge, presenting a relatively large surface contact area to the external acoustic meatus 45. Spreading the force exerted by the stethoscope over a large area provides the enhanced comfort exhibited by the ear tip 5 of the invention. Moreover, owing to the soft, elastic nature of the second section walls 23, the walls 23 are seen to conform closely to the irregular surface of the external acoustic meatus 45. In practice, the third section 11 of the ear tip 5, including the flange 47, enters the opening of the ear canal and together with second section 9, provides an acoustic seal. The result is substantial exclusion of ambient noise, which along with comfort is a critical requirement for a stethoscopic ear tip.

It is recognized that stethoscopic ear tubes often include threaded ends adapted to engage a complementary threaded bore in an ear tip. The ear tip of the present invention can be made amenable to use with such ear tubes by inserting into first section 7 an adapter with the requisite threaded bore.

Further, it is recognized that alternative embodiments of the invention may be useful for applications in addition to stethoscopes. For example, first section 7 may be adapted to accept a small acoustic speaker. Thus, the invention provides an ear tip suitable for use with audio headsets and electronic stethoscopes.

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following example are on a weight basis.

Two different size ear tips, currently available from 3M Company of St. Paul, Minn. were tested as comparative examples against two different embodiments of the current disclosure. Comparative Example 1 was 3M LITTMANN Snap Tight Soft-Sealing Eartip, black, size large (13.3 mm external diameter), catalog number 37811. Comparative Example 2 was 3M LITTMANN Snap Tight Soft-Sealing Eartip, black, size small (12.3 mm external diameter), catalog number 37809. Example 1 was a flume design ear tip of the current disclosure (FIGS. 2A and 2B), size small (12.3 mm external diameter of the second section 9). Example 2 was a flange design ear tip of the current disclosure (FIGS. 5A and 5B), size small (12.3 mm external diameter of the second section 9).

Figure 8:
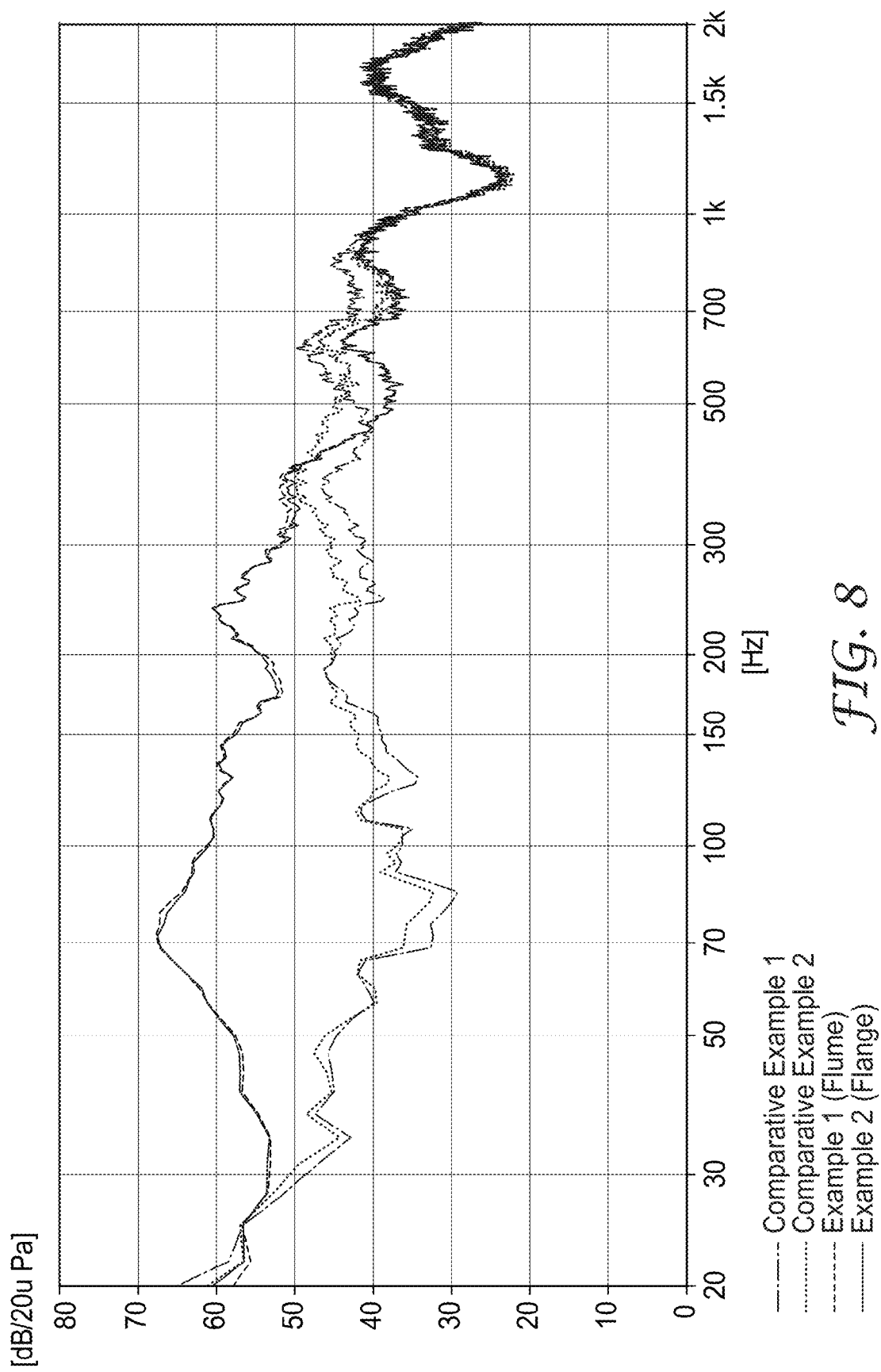
FIG. 8 is an autospectrum frequency response plot for stethoscopes using comparative examples and example embodiments of the current disclosure.

The examples were tested to produce the Frequency Response curves shown in FIG. 8. The comparison of the ear tip acoustic seal within the ear canal illustrates the quality of body sound measurements.

Figure 7:
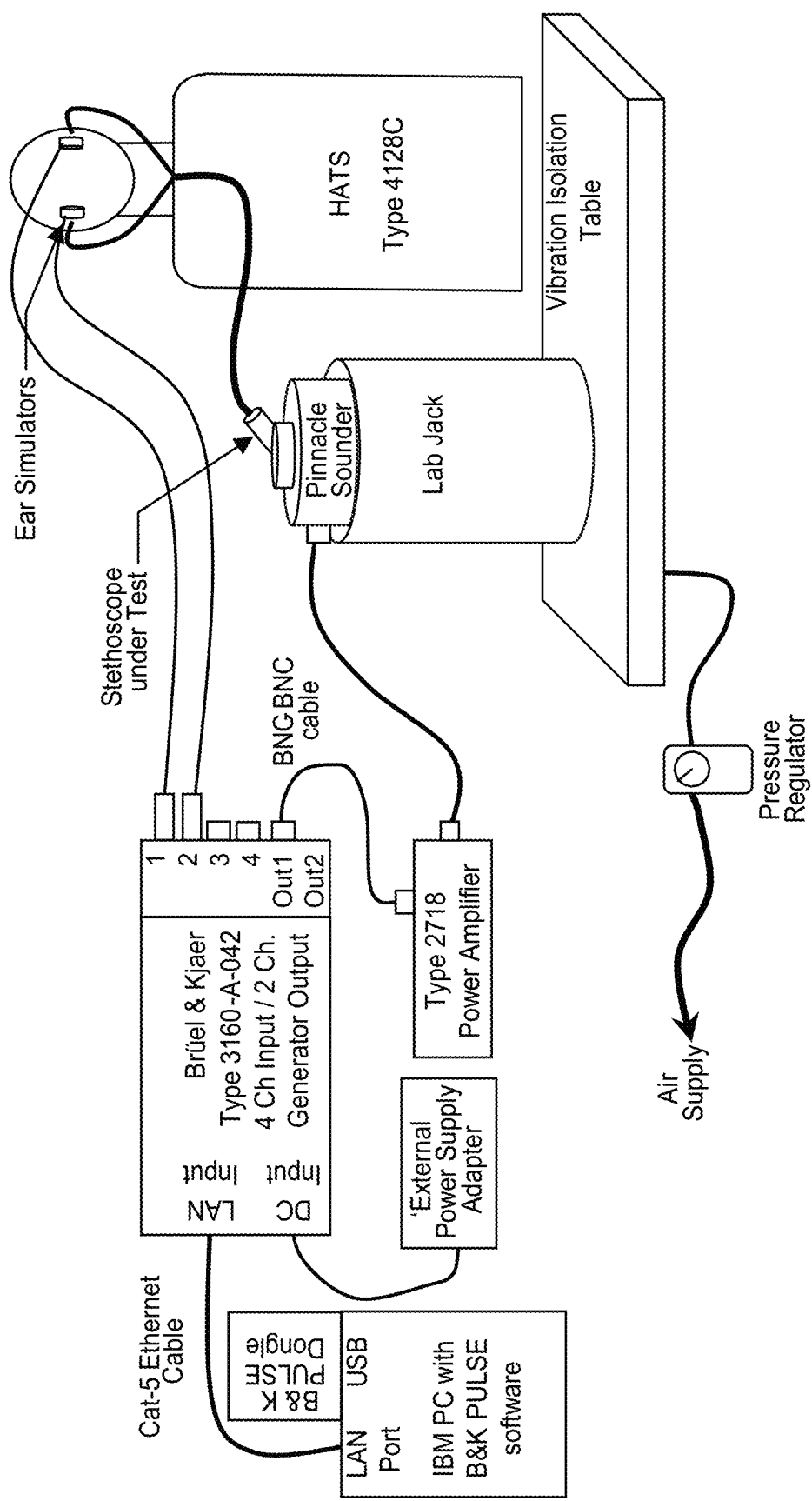
FIG. 7 is a diagram of a laboratory test set-up to generate an autospectrum frequency response of stethoscopes using the ear tips of the current invention.

During the testing all the example ear tips were connected to a 3M LITTMANN Classic II SE mechanical stethoscope. The testing setup was configured as shown in FIG. 7. The acoustic measurements were performed using Brüel & Kjær (B&K) PULSE software v 14.1.1 running on an IBM compatible desktop personal computer using Microsoft Windows 7 Professional operating system. The equipment included: Brüel & Kjær Head and Torso Simulator (HATS) type 4128C (with 4159C Left Ear Simulator, 4158C Right Ear Simulator, and Calibrated Left and Right pinnae); Power Amplifier Type 2718; Brüel & Kjær Type 3160-A-042 4 channel input/2 channel output generator; Pinnacle Technology Group, Inc. Sounder (SKU: FPL5090REV00); a 600 mm×900 mm Newport IsoStation Vibration Isolation Workstation; 35 PSI Pressure regulator; 50 gram brass weight for stethoscope.

An autospectrum frequency response measurement was performed by a B&K LAN-XI chassis supplying pink noise to the Pinnacle Sounder which was amplified by a Brüel & Kjær Type 2718 Power Amplifier.

As shown in FIG. 8, the flume and flange ear tips of Examples 1 and 2 performed better than the ear tips of Comparative Examples 1 and 2 across the critical 30-300 Hz range and had generally equivalent performance at the higher frequencies. This performance improvement is the result of a superior acoustic seal of the ear tips to the ear simulators.

Although the present invention has been described with reference to preferred embodiments, workers skilled in the art will recognize that changes may be made in form and detail without departing from the spirit and scope of the invention.

What is claimed is:

1. An ear tip adapted to deliver sound to an ear canal, the ear tip comprising:
   a first section connectable to a sound-transmitting device;
   a second section having a first end, a second end and walls defining a hollow bulbous section, wherein the first end is connected to and in open communication with the first section; and
   a third section connected to and in open communication with the second end of the second section, the third section comprising:
   walls defining a flume;
   an outlet port adapted for open communication with the ear canal, wherein the
   outlet port has a maximum outer diameter of about 11 millimeters (mm); and
   a flange extending from the outlet port;
   wherein in a relaxed state, a ratio of a maximum outer diameter of the second section to a maximum outer diameter of the third section is between about 1.25 and about 2.5.

2. The ear tip of claim 1, wherein the outlet port of the third section has a minimum outer diameter of about 5 mm.

3. The ear tip of claim 1, wherein the third section has a length of between about 2.5 to about 6.4 mm.

4. The ear tip of claim 1, wherein the outlet port of the third section is compressible to an oval shape, wherein a diameter of the oval is up to about 50% larger than the diameter of the outlet port in an uncompressed state.

5. The ear tip of claim 1, wherein the flange has an outer diameter of between about 8.1 and about 13.2 mm.

6. The ear tip of claim 1, wherein the flange has a dome height of between about 4 and about 8 mm.

7. The ear tip of claim 1, wherein the flange has a thickness of between about 0.3 and about 1.0 mm.

8. The ear tip of claim 1, further comprising a channel passing through the first section, wherein the channel is configured to receive a transmitting tube.

9. The ear tip of claim 1, wherein the second section comprises a hollow inner chamber.

10. The ear tip of claim 1, wherein the hollow inner chamber of the second section is positioned between the terminal end of the transmitting tube and the third section.

11. The ear tip of claim 1, wherein the sound-transmitting device is a stethoscope.

12. An ear tip comprising:
    a first section connectable to a sound-transmitting device;
    a second section having a first end, a second end and walls defining a hollow bulbous section surrounding an inner chamber, wherein the first end is connected to and in open communication with the first section; and
    a third section connected to and in open communication with the second end of the second section, the third section comprising walls defining a flume, wherein the flume includes a tip positionable within a human ear canal and wherein the flume has a length of about 2.5 to about 6.4 millimeters (mm);
    wherein the second and third sections are deformable under an axial force in a range of between about 2.22 to about 5.56 Newtons from a relaxed state to a compressed state and the flume tip exhibits a compression diameter increase of up to 50 %.

13. The ear tip of claim 12, wherein the flume tip has a maximum outer diameter of about 11 mm.

14. The ear tip of claim 12, wherein a ratio of a maximum outer diameter of the second section to a maximum outer diameter of the third section is between about 1.25 and about 2.5.

15. The ear tip of claim 12, wherein the third section further comprises a flange extending from the flume tip.

16. The ear tip of claim 15, wherein the flange has an outer diameter of between about 8.1 and about 13.2 mm.

17. The ear tip of claim 15, wherein the flange has a dome height of between about 3.8 and about 7.6 mm.

18. The ear tip of claim 15, wherein the flange has a thickness of between about 0.3 and about 1.0 mm.

19. The ear tip of claim 12, further comprising a channel passing through the first section, wherein the channel is configured to receive a transmitting tube.

20. The ear tip of claim 19, wherein the hollow inner chamber of the second section is positioned between the terminal end of the transmitting tube and the third section.

21. he ear tip of claim 12, wherein the sound-transmitting device is a stethoscope.

\* \* \* \* \*